United States Patent
Kim et al.

(10) Patent No.: US 12,325,683 B2
(45) Date of Patent: Jun. 10, 2025

(54) REMOVAL OF CARBON MONOXIDE, OXYGEN AND ACETYLENE FROM AN OXIDATIVE DEHYDROGENATION PROCESS

(71) Applicant: NOVA Chemicals (International) S.A., Fribourg (CH)

(72) Inventors: Yoonhee Kim, Calgary (CA); Xiaoliang Gao, Calgary (CA); Vasily Simanzhenkov, Calgary (CA); Bolaji Olayiwola, Calgary (CA); Shahin Goodarznia, Calgary (CA); David Gent, Red Deer (CA)

(73) Assignee: NOVA Chemicals (International) S.A., Fribourg (CH)

(*) Notice: Subject to any disclaimer, the term of this patent is extended or adjusted under 35 U.S.C. 154(b) by 0 days.

(21) Appl. No.: 17/785,562

(22) PCT Filed: Dec. 4, 2020

(86) PCT No.: PCT/IB2020/061522
§ 371 (c)(1),
(2) Date: Jun. 15, 2022

(87) PCT Pub. No.: WO2021/124004
PCT Pub. Date: Jun. 24, 2021

(65) Prior Publication Data
US 2023/0028068 A1 Jan. 26, 2023

Related U.S. Application Data

(60) Provisional application No. 62/951,209, filed on Dec. 20, 2019.

(51) Int. Cl.
*C07C 5/48* (2006.01)
*C07C 7/148* (2006.01)

(52) U.S. Cl.
CPC ............. *C07C 5/48* (2013.01); *C07C 7/148* (2013.01); *C07C 2523/06* (2013.01); *C07C 2523/72* (2013.01); *C07C 2523/80* (2013.01)

(58) Field of Classification Search
CPC ........ C07C 5/48; C07C 7/148; C07C 2523/06; C07C 2523/72; C07C 2523/80; C07C 11/04; Y02P 20/52
See application file for complete search history.

(56) References Cited

U.S. PATENT DOCUMENTS 3,549,719 A 12/1970 Duyverman et al.
3,754,050 A 8/1973 Duyverman et al.
(Continued)

FOREIGN PATENT DOCUMENTS

CN 105408291 3/2016
CN 109721459 5/2019
(Continued)

OTHER PUBLICATIONS

Anonymous, "Product Data Sheet: PuriStar R3-16 T5x3 (CuO/ZnO Tablets)," Retrieved from the Internet: URL: https://catalysts.basf.com/files/literature-library/BF-9226_A4_R3-16 Datasheet_Rev_2018-01_190411_120156.pdf, Jan. 1, 2018, 2 pages (Rev.02_2022).
(Continued)

*Primary Examiner* — Thuan D Dang
(74) *Attorney, Agent, or Firm* — Fish & Richardson P.C.

(57) ABSTRACT

A method of converting one or more alkanes to one or more alkenes that includes providing a first stream containing one or more alkanes and oxygen to an oxidative dehydrogenation reactor; converting at least a portion of the one or more alkanes to one or more alkenes in the oxidative dehydrogenation reactor to provide a second stream exiting the oxidative dehydrogenation reactor containing one or more alkanes, one or more alkenes, and one or more of oxygen,
(Continued)

carbon monoxide and acetylene; and providing the second stream to a second reactor containing a catalyst that includes CuO and ZnO and reacting the second stream to provide a third stream exiting the second reactor containing one or more alkanes, one or more alkenes, and lower or undetectable levels of oxygen and acetylene compared to the second stream.

18 Claims, 2 Drawing Sheets

(56) References Cited

U.S. PATENT DOCUMENTS

| | | | |
|---|---|---|---|
| 10,322,985 | B1 | 6/2019 | Lin et al. |
| 2003/0208085 | A1* | 11/2003 | Gaffney ............... B01J 35/612 |
| | | | 558/321 |
| 2013/0006030 | A1 | 1/2013 | Ahmed et al. |
| 2018/0305278 | A1* | 10/2018 | Serhal ............... B01D 53/1475 |
| 2019/0135715 | A1 | 5/2019 | Simanzhenkov et al. |

FOREIGN PATENT DOCUMENTS

| | | |
|---|---|---|
| CN | 110234431 | 9/2019 |
| CN | 110312697 | 10/2019 |
| CN | 110520400 | 11/2019 |
| WO | WO 2018153831 | 8/2018 |
| WO | WO 2019175731 | 9/2019 |

OTHER PUBLICATIONS

PCT International Search Report and Written Opinion in International Appln. No. PCT/IB2020/061522, mailed on Mar. 10, 2021, 11 pages.
CN Office Action in Chinese Appln. No. 202080087636.8, dated Oct. 27, 2023, 20 pages (with English translation).
CN Office Action in Chinese Appln. No. 202080087636.8, dated May 18, 2024, 21 pages (with English translation).
Li et al., "Application of Niobic Acid in Catalysis," Chemical Industry and Engineering, Jul. 2008, 25(4):359-364 (English Abstract).
JP Office Action in Japanese Appln. No. 2022-537377, dated Aug. 19, 2024, 7 pages (with English translation).

* cited by examiner

REMOVAL OF CARBON MONOXIDE, OXYGEN AND ACETYLENE FROM AN OXIDATIVE DEHYDROGENATION PROCESS

CROSS-REFERENCE TO RELATED APPLICATIONS

This application is a National Stage Application under 35 U.S.C. § 371 and claims the benefit of International Application No. PCT/IB2020/061522, filed Dec. 4, 2020, which claims priority to U.S. Application No. 62/951,209, filed Dec. 20, 2019, entitled REMOVAL OF CARBON MONOXIDE, OXYGEN AND ACETYLENE FROM AN OXIDATIVE DEHYDROGENATION PROCESS. The disclosures of the foregoing applications are incorporated herein by reference in their entirety.

The present disclosure relates generally to oxidative dehydrogenation (ODH) of lower alkanes into corresponding alkenes. In some embodiments, the present disclosure relates to controlling the carbon monoxide, oxygen and/or acetylene output levels from an ODH process.

Olefins like ethylene, propylene, and butylene, are basic building blocks for a variety of commercially valuable polymers. Since naturally occurring sources of olefins do not exist in commercial quantities, polymer producers rely on methods for converting the more abundant lower alkanes into olefins. The method of choice for today's commercial scale producers is steam cracking, a highly endothermic process where steam-diluted alkanes are subjected very briefly to a temperature of at least 800° C. The fuel demand to produce the required temperatures and the need for equipment that can withstand that temperature add significantly to the overall cost. Also, the high temperature promotes the formation of coke which accumulates within the system, resulting in the need for costly periodic reactor shut-down for maintenance and coke removal.

Oxidative dehydrogenation (ODH) is an alternative to steam cracking that is exothermic and produces little or no coke. In ODH a lower alkane, such as ethane, is mixed with oxygen in the presence of a catalyst to produce the corresponding alkene.

Other than in the operating examples or where otherwise indicated, all numbers or expressions referring to quantities of ingredients, reaction conditions, etc. used in the specification and claims are to be understood as modified in all instances by the term "about". Accordingly, unless indicated to the contrary, the numerical parameters set forth in the following specification and attached claims are approximations that can vary depending upon the desired properties, which the present disclosure desires to obtain. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, inherently contain certain errors necessarily resulting from the standard deviation found in their respective testing measurements.

Also, it should be understood that any numerical range recited herein is intended to include all sub-ranges subsumed therein. For example, a range of "1 to 10" is intended to include all sub-ranges between and including the recited minimum value of 1 and the recited maximum value of 10; that is, having a minimum value equal to or greater than 1 and a maximum value of equal to or less than 10. Because the disclosed numerical ranges are continuous, they include every value between the minimum and maximum values. Unless expressly indicated otherwise, the various numerical ranges specified in this application are approximations.

As used herein, the term "alkane" refers to an acyclic saturated hydrocarbon. In many cases, an alkane consists of hydrogen and carbon atoms arranged in a linear structure in which all of the carbon-carbon bonds are single bonds. Alkanes have the general chemical formula $C_nH_{2n+2}$. In many embodiments of the disclosure, alkane refers to one or more of ethane, propane, butane, pentane, hexane, octane, decane and dodecane. In particular embodiments, alkane refers to ethane and propane and, in some embodiments, ethane.

As used herein, the term "alkene" refers to unsaturated hydrocarbons that contain at least one carbon-carbon double bond. In many embodiments, alkene refers to alpha olefins. In many embodiments of the disclosure, alkene refers to one or more of ethylene, propylene, 1-butene, butadiene, pentene, pentadiene, hexene, octene, decene and dodecene. In particular embodiments, alkene refers to ethylene and propylene and, in some embodiments, ethylene.

As used herein, the terms "alpha olefin" or "α-olefin" refer to a family of organic compounds which are alkenes (also known as olefins) with a chemical formula $C_xH_{2x}$, distinguished by having a double bond at the primary or alpha (α) position. In many embodiments of the disclosure, alpha olefin refers to one or more of ethylene, propylene, 1-butene, 1-pentene, 1-hexene, 1-octene, 1-decene and 1-dodecene. In particular embodiments, alpha olefins refer to ethylene and propylene and, in some embodiments, ethylene.

As used herein, the term "diluent" refers to a gas that forms a non-explosive mixture with hydrocarbons or oxidation gasses. However, in some instances, the diluent may participate in the ODH reaction in the presence of an ODH catalyst. Further, in all instances, the diluent is used to remove heat so that the process remains outside of any flammable condition.

As used herein, the term "essentially free of oxygen" means the amount of oxygen present, if any, remaining in a process stream as described herein, is low enough that it will not present a flammability or explosive risk to the downstream process streams or equipment.

As used herein, the term "fixed bed reactor" refers to one or more reactors, in series or parallel, often including a cylindrical tube filled with catalyst pellets with reactants flowing through the bed and being converted into products. The catalyst in the reactor may have multiple configurations including, but not limited to, one large bed, several horizontal beds, several parallel packed tubes, and multiple beds in their own shells.

As used herein, the term "fluidized bed reactor" refers to one or more reactors, in series or parallel, often including a fluid (gas or liquid) which is passed through a solid granular catalyst, which can be shaped as tiny spheres, at high enough velocities to suspend the solid and cause it to behave as though it were a fluid.

As used herein, the term "gas phase polyethylene process" refers to a process where a mixture of ethylene, optional alpha olefin comonomers and hydrogen is passed over a catalyst in a fixed or fluidized bed reactor. The ethylene and optional alpha olefins polymerize to form grains of polyethylene, suspended in the flowing gas, which can pass out of the reactor. In some embodiments, two or more of the individual reactors are placed in parallel or in series, each of which are under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, and metallocene catalysts and combinations thereof.

As used herein, the term "HDPE" refers to high density polyethylene, which generally has a density of greater or equal to 0.941 g/cm$^3$. HDPE has a low degree of branching. HDPE is often produced using chromium/silica catalysts, Ziegler-Natta catalysts or metallocene catalysts.

As used herein, the term "high pressure polyethylene process" refers to converting ethylene gas into a white solid by heating it at very high pressures in the presence of minute quantities of oxygen (about <10 ppmv oxygen) at about 1000-3000 bar and at about 80-300° C. In many cases, the high pressure polyethylene process produces LDPE.

As used herein, the term "LDPE" refers to low density polyethylene, which is a polyethylene with a high degree of branching with long chains. Often, the density of a LDPE will range from 0.910-0.940 g/cm$^3$. LDPE is created by free radical polymerization.

As used herein, the term "linear velocity", in many cases the linear velocity of the gas stream (m/s), refers to the flow rate of a gas stream/cross-sectional surface area of the reactor/void fraction of the catalyst bed. In many cases the flow rate refers to the total of the flow rates of all the gases entering an ODH reactor, and is measured where the oxygen and alkane first contact an ODH catalyst and at the temperature and pressure at that point. The cross-section of the reactor is also measured at the entrance of the ODH catalyst bed. The "void fraction" of the catalyst bed refers to the volume of voids in the catalyst bed/total volume of the catalyst bed. The "volume of voids" refers to the voids between catalyst particles and does not include the volume of pores inside the catalyst particles. In many instances, the linear velocity can range from 5 cm/sec to 1500 cm/sec, in some instances from 10 cm/sec to 500 cm/sec.

As used herein, the term "LLDPE" refers to linear low density polyethylene, which is a polyethylene that can have significant numbers of short branches resulting from copolymerization of ethylene with at least one α-olefin comonomer. In some cases, LLDPE has a density in the range of 0.915-0.925 g/cm$^3$. In many cases, the LLDPE is an ethylene hexene copolymer, ethylene octene copolymer or ethylene butene copolymer. The amount of comonomer incorporated can be from 0.5 to 12 mole %, in some cases from 1.5 to 10 mole %, and in other cases from 2 to 8 mole % relative to ethylene.

As used herein, the term "long-chain branching" refers to a situation where during α-olefin polymerization, a vinyl terminated polymer chain is incorporated into a growing polymer chain. Long branches often have a length that is longer than the average critical entanglement distance of a linear (no long chain branching) polymer chain. In many cases long chain branching affects melt rheological behavior.

As used herein, the term "low pressure polyethylene process" refers to polymerizing ethylene using a catalyst that in many cases includes aluminum at generally lower pressures than the high pressure polyethylene process. In many cases the low pressure polyethylene process is carried out at about 10-80 bar and at about 70-300° C. In many cases the low pressure polyethylene process provides HDPE. In particular cases, an α-olefin comonomer is included in the low pressure polyethylene process to provide LLDPE.

As used herein, the term "MDPE" refers to medium density polyethylene, which is a polyethylene with some short and/or long chain branching and a density in the range of 0.926-0.940 g/cm$^3$. MDPE can be produced using chromium/silica catalysts, Ziegler-Natta catalysts or metallocene catalysts.

As used herein, the term "monomer" refers to small molecules containing at least one double bond that reacts in the presence of a free radical polymerization initiator to become chemically bonded to other monomers to form a polymer.

As used herein, the term "moving bed reactor" refers to reactors in which the catalytic material flows along with the reactants and is then separated from the exit stream and recycled.

As used herein, the term "MoVOx catalyst" refers to a mixed metal oxide having the empirical formula $Mo_{6.5-70}V_3O_d$, where d is a number to at least satisfy the valence of the metals; a mixed metal oxide having the empirical formula $Mo_{6.25-7.25}V_3O_d$, where d is a number to at least satisfy the valence of the metals, or combinations thereof.

As used herein, the term, "olefinic monomer" includes, without limitation, α-olefins, and in particular embodiments ethylene, propylene, 1-butene, 1-hexene, 1-octene and combinations thereof.

As used herein, the term, "oxidative dehydrogenation" or "ODH" refers to processes that couple the endothermic dehydration of an alkane with the strongly exothermic oxidation of hydrogen as is further described herein.

As used herein, the term "polyolefin" refers to a material, which is prepared by polymerizing a monomer composition containing at least one olefinic monomer.

As used herein, the term "polyethylene" includes, without limitation, homopolymers of ethylene and copolymers of ethylene and one or more α-olefins.

As used herein, the term "polypropylene" includes, without limitation, homopolymers of propylene, including isotactic polypropylene and syndiotactic polypropylene and copolymers of propylene and one or more α-olefins.

As used herein, the term "polymer" refers to macromolecules composed of repeating structural units connected by covalent chemical bonds and is meant to encompass, without limitation, homopolymers, random copolymers, block copolymers and graft copolymers.

As used herein, the term "short chain branching" refers to copolymers of ethylene with an α-olefin or with branches of less than about 40 carbon atoms. In many cases, the α-olefin or branches are present at less than 20 wt. %, in some cases less than 15 wt. % of the polyethylene. In many cases, the presence of short chain branches interferes with the formation of the polyethylene crystal structure and is observed as a lower density compared with a linear (no short chain branching) polyethylene of the same molecular weight.

As used herein, the term "solution polyethylene process" refers to processes that polymerize ethylene and one or more optional α-olefins in a mixture of lower alkane hydrocarbons in the presence of one or more catalysts. In some embodiments, two or more of the individual reactors are placed in parallel or in series, each of which can be under slightly different conditions, so that the properties of different polyethylenes from the reactors are present in the resulting polyethylene blend. In many cases the catalysts include, but are not limited to, chromium catalysts, Ziegler-Natta catalysts, zirconocene catalysts, hafnocene catalysts, phosphinimine catalysts and metallocene catalysts and combinations thereof.

As used herein, the term "slurry polyethylene process" refers to single-tube loop reactors, double-tube loop reactors or autoclaves (stirred-tank reactors) used to polymerize ethylene and optional α-olefins in the presence of a catalyst system and a diluent. Non-limiting examples of diluents include isobutane, n-hexane or n-heptane. In some embodiments, two or more of the individual reactors are placed in parallel or in series, each of which can be under slightly different conditions, so that the properties of different polyethylenes from the reactors are present in the resulting polyethylene blend. In many cases the catalyst system includes, but is not limited to, chromium catalysts, Ziegler-Natta catalysts, zirconocene catalysts, hafnocene catalysts, phosphinimine catalysts and metallocene catalysts and combinations thereof.

As used herein, the term "substantially free of acetylene" means the amount of acetylene present, if any, remaining in a process stream as described herein, is undetectable using the analytical techniques described herein or zero ppmv.

As used herein, the term "swing bed type reactor arrangement" is a gas phase reactor system where a first vessel effectively operates as a reactor and a second vessel effectively operates as a regenerator for regenerating the catalyst system. This arrangement can be used with fixed bed as well as fluidized bed gas phase polyethylene reactors.

As used herein, the term "thermoplastic" refers to a class of polymers that soften or become liquid when heated and harden when cooled. In many cases, thermoplastics are high-molecular-weight polymers that can be repeatedly heated and remolded. In many embodiments of the disclosure, thermoplastic resins include polyolefins and elastomers that have thermoplastic properties.

As used herein, the terms "thermoplastic elastomers" and "TPE" refer to a class of copolymers or a blend of polymers (in many cases a blend of a thermoplastic and a rubber) which includes materials having both thermoplastic and elastomeric properties.

As used herein, the terms "thermoplastic olefin" or "TPO" refer to polymer/filler blends that contain some fraction of polyethylene, polypropylene, block copolymers of polypropylene, rubber, and a reinforcing filler. The fillers can include, without limitation, talc, fiberglass, carbon fiber, wollastonite, and/or metal oxy sulfate. The rubber can include, without limitation, ethylene-propylene rubber, EPDM (ethylene-propylene-diene rubber), ethylene-butadiene copolymer, styrene-ethylene-butadiene-styrene block copolymers, styrene-butadiene copolymers, ethylene-vinyl acetate copolymers, ethylene-alkyl (meth)acrylate copolymers, very low density polyethylene (VLDPE) such as those available under the FLEXOMER® resin trade name from the Dow Chemical Co., Midland, MI, styrene-ethylene-ethylene-propylene-styrene (SEEPS). These can also be used as the materials to be modified by the interpolymer to tailor their rheological properties.

As used herein, the term "VLDPE" refers to very low density polyethylene, which is a polyethylene with high levels of short chain branching with a typical density in the range of 0.880-0.915 g/cc. In many cases VLDPE is a substantially linear polymer. VLDPE is typically produced by copolymerization of ethylene with α-olefins. VLDPE is often produced using metallocene catalysts.

As used herein, the term "weight hourly space velocity (WHSV)" refers to the gas flow in the ODH reactor in terms of the weight, as opposed to volume, of the gases that flow over the weight of the active catalyst per hour. In calculating WHSV the weight of the gases may include only the reactants but may also include diluents added to the gas mixture. In many embodiments of the disclosure, when including the weight of diluents, when used, the WHSV can range from 0.5 h$^{-1}$ to 50 h$^{-1}$, in many cases from 1.0 to 25.0 h$^{-1}$.

Unless otherwise specified, all molecular weight values are determined using gel permeation chromatography (GPC). Molecular weights are expressed as polyethylene equivalents with a relative standard deviation of 2.9% for the number average molecular weight ("Mn") and 5.0% for the weight average molecular weight ("Mw"). Unless otherwise indicated, the molecular weight values indicated herein are weight average molecular weights (Mw).

DESCRIPTION OF EMBODIMENTS

Figure 1:
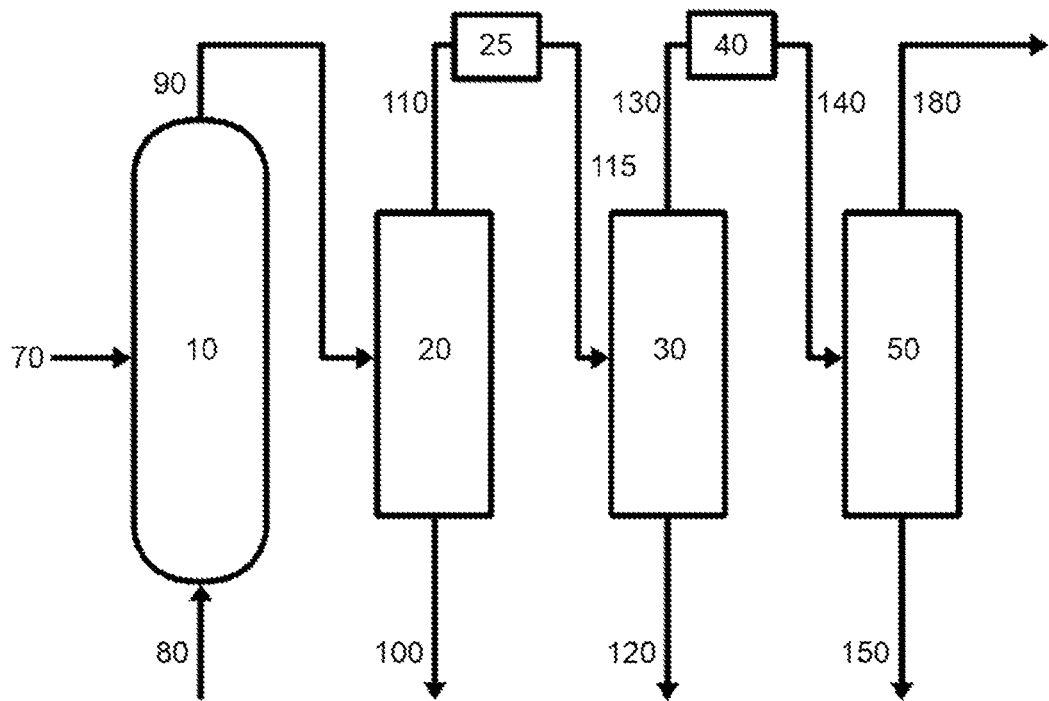
FIG. 1 is a schematic representation of chemical complex for oxidative dehydrogenation processes according to embodiments described herein.

In some embodiments disclosed herein, the degree to which carbon monoxide is produced during the ODH process can be mitigated by converting it to carbon dioxide, which can then act as an oxidizing agent. The process can be manipulated so as to control the output of carbon dioxide from the process to a desired level. Using the methods described herein a user may choose to operate in carbon dioxide neutral conditions such that surplus carbon dioxide need not be flared or released into the atmosphere.

In some embodiments disclosed herein, the degree to which acetylene is produced during the ODH process can be mitigated by converting it to other compounds.

In some embodiments disclosed herein, the degree to which oxygen is retained in post ODH process streams can be mitigated by converting it to other compounds.

Disclosed herein are methods for mitigating carbon monoxide and/or acetylene formation in an ODH process and minimizing the amount, if any, of oxygen in post ODH process streams. Aspects of the methods include introducing, into at least one ODH reactor, a gas mixture of a lower alkane, oxygen and optionally carbon dioxide, under conditions that allow production of the corresponding alkene and smaller amounts of various by-products. For multiple ODH reactors, each reactor contains the same or different ODH catalyst. In some embodiments a steam containing optional diluents may also be introduced into the reactor as part of the gas mixture.

In some embodiments the lower alkane is ethane, and the corresponding alkene is ethylene.

In further embodiments, at least one ODH reactor is a fixed bed reactor. In some embodiments at least one ODH reactor is a fixed bed reactor that includes heat dissipative particles within the fixed bed. In some embodiments the heat dissipative particles have a thermal conductivity that is greater than the catalyst. In alternative embodiments, at least one ODH reactor is a fluidized bed reactor.

In some embodiments, at least one ODH catalyst is a mixed metal oxide catalyst. In particular embodiments, at least one ODH catalyst is a mixed metal oxide of the formula: $MO_aV_bTe_cNb_dPd_eO_f$ wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals in the catalyst.

In other particular embodiments, at least one ODH catalyst is a mixed metal oxide of the formula:

$$Mo_{6.25-7.25}V_3O_d$$

where d is a number to at least satisfy the valence state of the metals.

Various embodiments relate to oxidative dehydrogenation (ODH) of lower alkanes into corresponding alkenes. Lower alkanes are saturated hydrocarbons with from 2 to 4 carbons, and the corresponding alkene includes hydrocarbons with the same number of carbons, but with one carbon to carbon double bond. While any of the lower alkanes can be converted to their corresponding alkenes using the methods disclosed herein, one particular embodiment is the ODH of ethane, producing its corresponding alkene, ethylene.

The ODH Process

ODH of alkanes includes contacting a mixture of one or more alkanes and oxygen in an ODH reactor with an ODH catalyst under conditions that promote oxidation of the alkanes into their corresponding alkenes. Conditions within the reactor are controlled by the operator and include, but are not limited to, parameters such as temperature, pressure, and flow rate. Conditions will vary and can be optimized for a particular alkane, or for a specific catalyst, or whether an diluent is used in the mixing of the reactants.

Use of an ODH reactor for performing an ODH process consistent with the disclosure falls within the knowledge of the person skilled in the art. For best results, the oxidative dehydrogenation of one or more alkanes may be conducted at temperatures from 300° C. to 500° C., or from 300° C. to 450° C., or from 330° C. to 425° C., at pressures from 0.5 to 100 psig (3.447 to 689.47 kPag), or from 15 to 50 psig (103.4 to 344.73 kPag), and the residence time of the one or more alkanes in the reactor may be from 0.002 to 30 seconds, or from 1 to 10 seconds.

In some embodiments, the process has a selectivity for the corresponding alkene (ethylene in the case of ethane ODH) of greater than 95%, or for example, greater than 98%. The gas hourly space velocity (GHSV) can be from about 400 to about 30000 $h^{-1}$, or greater than 1000 $h^{-1}$. In some embodiments, the gas velocity can be described in terms of weight hourly space velocity (WHSV), which can be from about 0.4 $h^{-1}$ to about 30 $h^{-1}$. In some embodiments the gas velocity can be described in terms of linear velocity, which can be from about 5 cm/sec to about 500 cm/sec. In some embodiments, the space-time yield of corresponding alkene (productivity) in g/hour per kg of the catalyst can be at least 50 or above, or greater than 1500, or greater than 3000, or greater than 3500, at 330 to 500° C., depending on the temperature profile in the catalyst bed. In some embodiments, the productivity of the catalyst will increase with increasing temperature until the selectivity is decreased.

ODH Catalyst

Any of the ODH catalysts known in the art are suitable for use in the methods disclosed herein. Non-limiting examples of suitable oxidative dehydrogenation catalyst include those containing one or more mixed metal oxides selected from:

i) catalysts of the formula:

$$MO_aV_bTe_cNb_dPd_eO_f$$

where a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals in the catalyst;

ii) catalysts of the formula:

$$Ni_gA_hB_iD_jO_f$$

where g is a number from 0.1 to 0.9, in many cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, TI, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_aE_kG_lO_f$$

where E is chosen from Ba, Ca, Cr, Mn, Nb, Ta, Ti, Te, V, W and mixtures thereof; chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to at least satisfy the valence state of the metals in the catalyst;

iv) catalysts of the formula:

$$V_mMo_nNb_oTe_pMe_qO_f$$

where Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals in the catalyst; and v) catalysts of the formula:

$$MO_aV_rX_sY_tZ_uM_vO_f$$

where X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst.

When choosing a catalyst, those skilled in the art can appreciate that catalysts may vary with respective to selectivity and activity. Some embodiments of ODH of ethane in this disclosure use a mixed metal oxide catalysts that can provide high selectivity to ethylene without significant loss in activity. Non-limiting example catalysts are those of the formula:

$$MO_aV_bTe_cNb_dPd_eO_f$$

wherein a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals in the catalyst.

vi) a mixed metal oxide having the empirical formula:

$$Mo_{6.5-7}V_3O_d$$

where d is a number to at least satisfy the valence of the metals in the catalyst.

vii) a mixed metal oxide having the empirical formula:

$$Mo_{6.25-7.25}V_3O_d$$

where d is a number to at least satisfy the valence of the metals in the catalyst.

In some embodiments, the catalyst may be supported on/agglomerated with a binder. Some binders include acidic, basic or neutral binder slurries of $TiO_2$, $ZrO_2$ $Al_2O_3$, AlO (OH) and mixtures thereof. Another useful binder includes $Nb_2O_5$. The agglomerated catalyst may be extruded in a suitable shape (rings, spheres, saddles etc.) of a size typically used in fixed bed reactors. When the catalyst is extruded, various extrusion aids known in the art can be used. In some cases, the resulting support may have a cumulative surface area of less than 35 $m^2/g$ as measured by BET, in some cases, less than 20 $m^2/g$, in other cases, less than 3 $m^2/g$. and a cumulative pore volume from 0.05 to 0.50 $cm^3/g$.

ODH Reactor

Any of the known reactor types applicable for the ODH of alkanes may be used with the methods disclosed herein. In some embodiments, the methods may be used with conventional fixed bed reactors. In a typical fixed bed reactor, reactants are introduced into the reactor at one end, flow past an immobilized catalyst, products are formed and leave at the other end of the reactor. Designing a fixed bed reactor suitable for the methods disclosed herein can follow techniques known for reactors of this type. A person skilled in the art would know which features are required with respect to shape and dimensions, inputs for reactants, outputs for products, temperature and pressure control, and means for immobilizing the catalyst.

In some embodiments, the use of inert non-catalytic heat dissipative particles can be used within one or more of the ODH reactors. In various embodiments, the heat dissipative particles are present within the bed and include one or more non catalytic inert particulates having a melting point at least 30° C., in some instances at least 100° C. in some embodiments at least 250° C., in further embodiments at least 500° C. above the temperature upper control limit for the reaction; a particle size in the range of about 0.1 mm to about 50 mm, in some embodiments 0.5 mm to 15 mm, in further embodiments in the range of 0.5 mm to 8 mm, in other embodiments in the range of 0.5 mm to 5 mm; and a thermal conductivity of greater than 10 W/mK (watts/meter Kelvin) within the reaction temperature control limits. In some embodiments the particulates are metal alloys and compounds having a thermal conductivity of greater than 10 W/mK (watts/meter Kelvin) within the reaction temperature control limits. Non-limiting examples of suitable metals that can be used in these embodiments include, but are not limited to, silver, copper, gold, aluminum, steel, stainless steel, molybdenum, and tungsten.

The heat dissipative particles can have a particle size of from about 1 mm to about 15 mm. In some embodiments, the particle size can be from about 0.1 mm to about 50 mm, in some embodiments 0.5 mm to 15 mm, in other embodiments in the range of 0.5 mm to 8 mm, in further embodiments in the range of 0.5 mm to 5 mm. The heat dissipative particles can be added to the fixed bed in an amount from 5 to 95 wt. %, in some embodiments from 30 to 70 wt. %, in other embodiments from 45 to 60 wt. % based on the entire weight of the fixed bed. The particles are employed to potentially improve cooling homogeneity and reduction of hot spots in the fixed bed by transferring heat directly to the walls of the reactor.

Additional embodiments include the use of a fluidized bed reactor, where the catalyst bed can be supported by a porous structure, or a distributor plate, located near a bottom end of the reactor and reactants flow through at a velocity sufficient to fluidize the bed (e.g. the catalyst rises and begins to swirl around in a fluidized manner). The reactants are converted to products upon contact with the fluidized catalyst and the reactants are subsequently removed from the upper end of the reactor. Design considerations those skilled in the art can modify and optimize include, but are not limited to, the shape of the reactor, the shape and size of the distributor plate, the input temperature, the output temperature, and reactor temperature and pressure control.

Embodiments of the disclosure include using a combination of both fixed bed and fluidized bed reactors, each with the same or different ODH catalyst. The multiple reactors can be arrayed in series or in parallel configuration, the design of which falls within the knowledge of the worker skilled in the art.

Oxygen/Alkane Mixture

In many embodiments, mixtures of one or more alkanes with oxygen should be employed using ratios that fall outside of the flammability envelope of the one or more alkanes and oxygen. In some embodiments, the ratio of alkanes to oxygen may fall outside the upper flammability envelope. In these embodiments, the percentage of oxygen in the mixture can be less than 30 vol %, in some cases less than 25 vol %, or in other cases less than 20 vol %, but greater than zero or at least 0.1 vol %.

In embodiments with higher oxygen percentages, alkane percentages can be adjusted to keep the mixture outside of the flammability envelope. While a person skilled in the art would be able to determine an appropriate ratio level, in many cases the percentage of oxygen is less than about 40 vol % and greater than zero or at least 0.1 vol %. As a non-limiting example, where the mixture of gases prior to ODH includes 10 vol % oxygen and 15 vol % alkane, the balance can be made up with a diluent. Non-limiting examples of useful diluents in this embodiment include, but are not limited to, one or more of nitrogen, carbon dioxide, and steam. In some embodiments, the diluent should exist in the gaseous state at the conditions within the reactor and should not increase the flammability of the hydrocarbon added to the reactor, characteristics that a skilled worker would understand when deciding on which diluent to employ. The diluent can be added to either of the alkane containing gas or the oxygen containing gas prior to entering the ODH reactor or may be added directly into the ODH reactor.

In embodiments of the disclosure, the volumetric feed ratio of oxygen to ethane ($O_2/C_2H_6$) provided to the one or more ODH reactors can be at least about 0.1, in some instances about 0.2, in other instances about 0.3, in some cases at least about 0.4, and in other cases at least about 0.5 and can be up to about 1, in some cases up to about 0.9, in other cases up to about 0.8, in some instances up to about 0.7 and in other instances up to about 0.6. The volumetric feed ratio of oxygen to ethane can be any of the values or range between any of the values recited above.

In some embodiments mixtures that fall within the flammability envelope may be employed, as a non-limiting example, in instances where the mixture exists in conditions that prevent propagation of an uncontrolled process. In these non-limiting examples, the flammable mixture is created within a medium where ignition is immediately quenched. As a further non-limiting example, a user may design a reactor where oxygen and the one or more alkanes are mixed at a point where they are surrounded by a flame arresting material. Any ignition would be quenched by the surrounding material. Flame arresting materials include, but are not limited to, metallic or ceramic components, such as stainless steel walls or ceramic supports. In some embodiments, oxygen and alkanes can be mixed at a low temperature, where an ignition event would not lead to an uncontrolled process, then introduced into the reactor before increasing the temperature. The flammable conditions do not exist until the mixture is surrounded by the flame arrestor material inside of the reactor.

Carbon Monoxide Output

Carbon monoxide can be produced in the ODH reaction as a by-product of oxidation of the one or more alkanes. The carbon monoxide output is a function of the amount of carbon monoxide produced in the oxidative process.

Measuring the amount of carbon monoxide coming off the ODH reactor can be done using any means known in the art. For example, one or more detectors such as GC, IR, or Rahman detectors, are situated immediately downstream of the reactor to measure the carbon monoxide output. While not required, the output of other components may also be measured. These include but are not limited to the amounts of ethylene, unreacted ethane, acetylene, carbon dioxide and oxygen, and by-products such as acetic acid.

Carbon monoxide output can be stated using any metric commonly used in the art. For example, the carbon monoxide output can be described in terms of mass flow rate (g/min) or volumetric flow rate ($cm^3$/min). In some embodiments, normalized selectivity can be used to assess the degree to which carbon monoxide is produced or consumed. In that instance the net mass flow rate of CO—the difference between the mass flow rate of CO entering and leaving the ODH reactor—is normalized to the conversion of ethane, in essence describing what fraction of ethane is converted into carbon monoxide as opposed to ethylene, or other by-products such as acetic acid.

Many industrial processes, in addition to ODH, produce carbon monoxide which must be captured or flared where it contributes to the emission of greenhouse gases. Using the carbon monoxide mitigation steps disclosed herein converts most, if not all, carbon monoxide resulting from the ODH process to carbon dioxide. An advantage then is the ability to reduce or eliminate the amount of carbon monoxide produced in the ODH process in combination with other processes, such as thermal cracking. In some instances, the carbon dioxide can be captured in the amine wash tower.

Acetylene Output

Acetylene can be produced in the ODH reaction as a by-product of oxidation of the one or more alkanes. The acetylene output is a function of the amount of acetylene produced in the oxidative process.

Measuring the amount of acetylene coming off the ODH reactor can be done using any means known in the art. For example, one or more detectors such as GC, IR, or Rahman detectors, are situated immediately downstream of the reactor to measure the acetylene output. While not required, the output of other components may also be measured. These include but are not limited to the amounts of ethylene, unreacted ethane, carbon monoxide, carbon dioxide and oxygen, and by-products such as acetic acid.

Acetylene output can be stated using any metric commonly used in the art. For example, the acetylene output can be described in terms of mass flow rate (g/min), volumetric flow rate ($cm^3$/min) or volumetric parts per million (ppmv). In some embodiments, normalized selectivity can be used to assess the degree to which acetylene is produced or consumed. In that instance the net mass flow rate of acetylene—the difference between the mass flow rate of acetylene entering and leaving the ODH reactor—is normalized to the conversion of ethane, in essence describing what fraction of ethane is converted into acetylene as opposed to ethylene, or other by-products such as acetic acid.

Using the acetylene mitigation steps disclosed herein reacts most, if not all, acetylene resulting from the ODH process. An advantage then is the ability to reduce or eliminate the amount of acetylene produced in the ODH process in combination with other processes, such as thermal cracking and eliminate downstream unit operations in an ODH-type process.

Removal of Carbon Monoxide, Acetylene and Oxygen

Carbon monoxide, oxygen and acetylene are contaminants, that can affect the performance of equipment downstream of the one or more ODH reactors and/or have a negative impact on the purity of the final ethylene product. A reactor placed downstream of the one or more ODH reactors containing a catalyst material that includes CuO and ZnO removes all or part of the carbon monoxide, oxygen and acetylene in the process stream passing through. In some embodiments, the material that includes CuO and ZnO can act as an adsorbent for carbon monoxide, oxygen and acetylene. In other embodiments, the material that includes CuO and ZnO can perform as a selective carbon monoxide oxidation catalyst.

In some embodiments, after a bed of material that includes CuO and ZnO is depleted of chemosorbed oxygen the material can initiate a chemical reaction whereby oxygen and acetylene are removed or eliminated, without removing carbon monoxide from the process stream. Not being limited by any single theory, it is believed that in this embodiment, CuO and ZnO are reduced to their corresponding elemental metal forms via the reaction.

When the above described reactor containing a catalyst material that includes CuO and ZnO is placed downstream of the one or more ODH reactors, the mode of operation can be beneficial in certain integration options of ODH with different plants where carbon monoxide is a preferred feedstock for downstream plants as compared to carbon dioxide.

Carbon Dioxide Output

Carbon dioxide can be produced in the ODH reaction as a by-product of oxidation of the alkanes and recycled from the oxidation of carbon monoxide. Carbon dioxide can also be added into the ODH reactor when used as an inert diluent. Conversely, carbon dioxide may be consumed when it acts as an oxidant for the dehydrogenation reaction. The carbon dioxide output is therefore a function of the amount of carbon dioxide added and produced minus that consumed in the oxidative process. In some embodiments, the disclosed methods control the degree to which carbon dioxide acts as an oxidizing agent so as to impact the overall carbon dioxide output coming out of the ODH process.

Measuring the amount of carbon dioxide coming out of the ODH process can be done using any means known in the art. For example, one or more detectors such as GC, IR, or Rahman detectors, are situated immediately downstream of the reactor to measure the carbon dioxide output. While not required, the output of other components may also be measured. These include but are not limited to the amounts of ethylene, unreacted ethane, carbon monoxide and oxygen, and by-products such as acetic acid. Also, it should be noted that depending on the chosen metric for carbon dioxide output, the output levels of the other components, for example ethane, may actually be required.

Carbon dioxide output can be stated using any metric commonly used in the art. For example, the carbon dioxide output can be described in terms of mass flow rate (g/min) or volumetric flow rate ($cm^3$/min). In some embodiments, normalized selectivity can be used to assess the degree to which carbon dioxide is produced or consumed. In that instance, the net mass flow rate of $CO_2$—the difference between the mass flow rate of $CO_2$ entering and leaving the ODH reactor—is normalized to the conversion of ethane, in essence describing what fraction of ethane is converted into carbon dioxide as opposed to ethylene, or other by-products such as acetic acid. A carbon selectivity of 0 indicates that the amount of carbon dioxide entering the reactor is the same as the carbon dioxide output. In other words, the process is carbon dioxide neutral. A positive carbon dioxide selectivity alerts a user that carbon dioxide is being produced, and that any oxidation of carbon dioxide that is occurring is insufficient to offset that production, resulting in the process being carbon dioxide positive which may result in a lower selectivity for the olefin.

In some embodiments of the disclosure, product selectivity for carbon dioxide is less than about 10 wt. %, in some cases less than about 7.5 wt. % and in other cases less than about 5 wt. %. The product selectivity for carbon dioxide can be any of the values or range between any of the values recited above.

In some embodiments, the total amount of carbon dioxide in the stream exiting the one or more ODH reactors can be essentially the same as the total amount of carbon dioxide in the stream entering the one or more ODH reactors. In this instance, essentially the same means that the difference between the amount of carbon dioxide in the stream exiting the ODH reactors is within 2 volume percent (+2 vol %) of the amount of carbon dioxide entering the ODH reactors. In particular embodiments of the disclosure, the amount of carbon dioxide in the stream exiting the ODH reactors can be about +5 vol %, in some cases about +7.5 vol % and in other cases about +10 vol % and can be about −5 vol %, in some cases about +7.5 vol % and in other cases about −10 vol % of the amount of carbon dioxide in the stream entering the ODH reactors. The difference between the amount of carbon dioxide in the stream exiting the ODH reactors and the amount of carbon dioxide entering the ODH reactors can be any value or range between any of the values recited above.

In some embodiments, the methods and apparatus disclosed herein provide the possibility of a carbon dioxide negative process. In this instance, carbon dioxide is consumed at a higher rate than it is produced and shows a negative carbon selectivity. The ODH process may produce carbon dioxide, but the degree to which carbon dioxide is consumed while acting as an oxidizing agent offsets any production that is occurring. Many industrial processes, in addition to ODH, produce carbon dioxide which must be captured or flared where it contributes to the emission of greenhouse gases. When using a carbon dioxide negative process, the excess carbon dioxide from other processes may be captured and used as the diluent in the ODH process under conditions where there is negative carbon selectivity. An advantage then is the ability to reduce the amount of carbon dioxide produced in the ODH process in combination with other processes, such as thermal cracking. In addition, consumption of carbon dioxide is endothermic and by increasing the degree to which carbon dioxide acts as an oxidizing agent, heat produced from ODH of ethane is partially offset by consumption of carbon dioxide, reducing the degree to which heat must be removed from the reactor. In some embodiments, when acting as an oxidizing agent, carbon dioxide can produce carbon monoxide, which can be captured and used as an intermediate in production of other chemical products, such as methanol or formic acid.

Acetic Acid Removal

The stream exiting the one or more ODH reactors can be directed to a quench tower or acetic acid scrubber, in some cases, prior to being fed to the second reactor, which facilitates removal of oxygenates, such as acetic acid, ethanol and water via a bottom outlet. A stream containing unconverted lower alkane (such as ethane), corresponding alkene (such as ethylene), and one or more of unreacted oxygen, carbon dioxide, carbon monoxide, acetylene and inert diluent, are allowed to exit the scrubber and are fed downstream.

In embodiments of the disclosure, the stream from the one or more ODH reactors is cooled to a lower temperature prior to being fed to an acetic acid scrubber (as described below). The temperature of the stream prior to entering the acetic acid scrubber can be at least about 40° C., in some cases at least about 45° C., and in other cases at least about 50° C. and can be up to about 90° C., in some cases up to about 85° C., in other cases up to about 80° C., in some instances up to about 75° C. and in other instances up to about 70° C. The temperature of the ODH reactor product stream fed to an acetic acid scrubber can be cooled to any temperature value or range between any of the temperature values recited above.

The oxygenates removed via the quench tower or acetic acid scrubber can include carboxylic acids (for example acetic acid), aldehydes (for example acetaldehyde), alcohols (for example thanol) and ketones (for example acetone).

The amount of oxygenate compounds remaining in the stream exiting the scrubber will often be zero, i.e, below the detection limit for analytical test methods typically used to detect such compounds. When oxygenates can be detected they can be present at a level of up to about 1 per million by volume (ppmv), in some cases up to about 5 ppmv, in other cases less than about 10 ppmv, in some instances up to about 50 ppmv and in other instances up to about 100 ppmv and can be present up to about 2 vol %, in some cases up to about 1 vol %, and in other cases up to about 1,000 ppmv. The amount of oxygenates or acetic acid in the stream exiting the scrubber can be any value, or range between any of the values recited above.

The Second Reactor

In many embodiments, the ODH reactor (or reactors) can provide a stream containing at least a small amount of oxygen remaining as reactor effluent. In embodiments of the disclosure, the oxygen can provide a benefit to the ODH reactor product gas. In some embodiments, when the ODH catalyst is exposed to an oxygen free reducing environment at elevated temperature, it may become permanently degraded. In other embodiments, if the level of oxygen in the product gas from the ODH reactor contains less than about 1 ppmv of oxygen, most, if not all, of the one or more alkanes are converted to one or more alkenes in the inlet portion of the reactor and a large portion of the reactor catalyst bed is not utilized.

In other embodiments, oxygen in the ODH reactor product gas causes serious and operational issues in the downstream equipment, as a non-limiting example, at the first compression stage of an ODH process. This process consideration presents a need to remove oxygen to a very low or non-detectable level before the product gas is compressed.

One method used to reduce/eliminate oxygen in the ODH product gas focuses on catalytically combusting a small portion of the ODH product gas to the complete consumption of any residual oxygen. This approach is viable, however, in many cases it is undesirable, because it increases the overall oxygen consumption in the ODH process and, in the non-limiting example of the alkane being ethane, reduces overall process selectivity toward ethylene.

As described above, a reactor placed downstream of the one or more ODH reactors containing a catalyst material that includes CuO and ZnO removes all or part of the carbon monoxide, oxygen and acetylene in the process stream passing through. In some embodiments, the material that includes CuO and ZnO can act as an adsorbent for carbon monoxide, oxygen and acetylene. In other embodiments, the material that includes CuO and ZnO can perform as a selective carbon monoxide oxidation catalyst.

In embodiments of the disclosure, the amount of oxygen in the stream leaving the one or more ODH reactors can be at least about 80 ppmv, in some cases at least about 100 ppmv, in other cases at least about 150 ppmv and in some instances at least about 200 ppmv and can be up to about 5 vol %, in some cases up to about 4 vol %, in other cases up to about 3 vol %, in some instances up to about 2 vol %, in other instances up to about 1 vol %, and in particular situations up to about 500 ppmv. The amount of oxygen in the stream leaving the one or more ODH reactors can be any of the values or range between any of the values recited above.

In embodiments of the disclosure, when there is oxygen in the stream leaving the second reactor (in some instances the amount of oxygen will be undetectable or zero ppmv), the amount of oxygen in the stream leaving the second reactor can be at least about 1 ppmv, in some cases at least about 2 ppmv, in other cases at least about 3 ppmv and in some instances at least about 5 ppmv and can be up to about 1 vol %, in some cases up to about 0.9 vol %, in other cases up to about 0.8 vol %, in some instances up to about 0.7 vol %, in other instances up to about 0.6 vol %, and in particular situations up to about 0.5 vol %. The amount of oxygen in the stream leaving the second reactor can be any of the values or range between any of the values recited above.

In embodiments of the disclosure, the amount of carbon monoxide in the stream leaving the one or more ODH reactors can be at least about 100 ppmv, in some cases at least about 200 ppmv, in other cases at least about 300 ppmv and in some instances at least about 400 ppmv and can be up to about 10 vol %, in some cases up to about 9 vol %, in other cases up to about 8 vol %, in some instances up to about 7 vol %, in other instances up to about 6 vol %, and in particular situations up to about 5 vol %. The amount of carbon monoxide in the stream leaving the one or more ODH reactors can be any of the values or range between any of the values recited above.

In embodiments of the disclosure, when there is carbon monoxide in the stream leaving the second reactor (in some instances the amount of carbon monoxide will be undetectable or zero ppmv), the amount of carbon monoxide in the stream leaving the second reactor can be at least about 1 ppmv, in some cases at least about 2 ppmv, in other cases at least about 3 ppmv and in some instances at least about 5 ppmv and can be up to about 8 vol %, in some cases up to about 7 vol %, in other cases up to about 6 vol %, in some instances up to about 5 vol %, in other instances up to about 4 vol %, and in particular situations up to about 3 vol %. The amount of carbon monoxide in the stream leaving the second reactor can be any of the values or range between any of the values recited above.

In embodiments of the disclosure, when there is acetylene in the stream leaving the one or more ODH reactors (in some instances the amount of acetylene will be undetectable or zero ppmv), the amount of acetylene in the stream leaving the one or more ODH reactors can be at least about 1 ppmv, in some cases at least about 2 vppm, in other cases at least about 5 ppmv and in some instances at least about 10 ppmv and can be up to about 1000 ppmv, in some cases up to about 750 ppmv, in other cases up to about 500 ppmv, in some instances up to about 400 ppmv, in other instances up to about 300 ppmv, and in particular situations up to about 300 ppmv. The amount of acetylene in the stream leaving the one or more ODH reactors can be any of the values or range between any of the values recited above.

In embodiments of the disclosure, the amount of acetylene in the stream leaving the second reactor will be less than the amount entering the second reactor and, in many instances, the stream exiting the second reactor will be substantially free of acetylene.

In embodiments of the disclosure, when there is acetylene in the stream leaving the second reactor (in many instances the amount of acetylene will be undetectable, less than 1 ppmv, or zero ppmv), the amount of acetylene in the stream leaving the second reactor can be at least about 1 ppmv, in some cases at least about 2 ppmv, in other cases at least about 3 ppmv and in some instances at least about 5 ppmv and can be up to about 100 ppmv, in some cases up to about 50 ppmv, in other cases up to about 25 ppmv, in some instances up to about 20 ppmv, in other instances up to about 15 ppmv, and in particular situations up to about 10 ppmv. The amount of acetylene in the stream leaving the second reactor can be any of the values or range between any of the values recited above.

In embodiments of the disclosure, temperature in the second reactor can be at least about 100, in some cases at least about 110, in other cases at least about 115 and in some instances at least about 120° C. and can be up to about 200, in some instances up to about 190, in other instances up to about 180, in some circumstances up to about 175, and in other circumstances up to about 170° C. The temperature of second reactor can be any temperature value or range between any of the temperature values, including a temperature gradient within the second reactor, recited above.

In various embodiments of the disclosure, a fixed bed reactor loaded with a catalyst material that includes CuO and ZnO, can be located in three different locations in the ODH process:

At the ODH reactor outlet, whereby the product from the reactor outlet can be cooled to below 200° C., before it enters the second reactor.

At the outlet of the acetic acid scrubber/quench tower, whereby the gaseous feed to the second reactor can be preheated to at least 100° C.

At the outlet of the first stage compression of the gaseous ODH product, downstream of the acetic acid scrubber, whereby the feed to the second reactor can be, at least, in part preheated by the energy of the compression.

ODH Complex

In the following description of the present disclosure for reference to the figures it should be noted that like parts are designated by like reference numbers.

In embodiments of the disclosure, the chemical complex of the present disclosure, shown in one embodiment schematically in FIG. 1, includes, in cooperative arrangement, an ODH reactor 10, a quench tower or acetic acid scrubber 20, a second reactor 25 (as described herein), an amine wash tower 30 (which can include a caustic tower), a drier 40, and a distillation tower 50 (this is $C_1$ column). There should another column for separating ethylene and ethane since there is not going to be 100% ethane conversion. ODH reactor 10 includes an ODH catalyst capable of catalyzing, in the presence of oxygen which may be introduced via oxygen line 70, the oxidative dehydrogenation of alkanes introduced via alkane line 80. Although second reactor 25 is shown directly after quench tower or acetic acid scrubber 20, in many instances it will be more efficiently utilized after the gas stream is compressed, in many cases prior to amine wash tower 30. Thus, in many cases, the process configuration can be more energy efficient if second reactor 25 is placed after the input stream has been compressed.

The ODH reaction may also occur in the presence of an inert diluent, such as carbon dioxide, nitrogen, or steam, that is added to ensure the mixture of oxygen and hydrocarbon are outside of flammability limits. Determination of whether a mixture is outside of the flammability limits, for the prescribed temperature and pressure, is within the knowledge of the skilled worker. An ODH reaction that occurs within ODH reactor 10 may also produce, depending on the catalyst and the prevailing conditions within ODH reactor 10, a variety of other products which may include carbon dioxide, carbon monoxide, oxygenates, and water. These products leave ODH reactor 10, along with unreacted alkane, corresponding alkene, residual oxygen, carbon monoxide, acetylene and inert diluent, if added, via ODH reactor product line 90.

ODH reactor product line 90 is directed to quench tower or acetic acid scrubber 20 which quenches the products from product line 90 and facilitates removal of oxygenates and water via quench tower bottom outlet 100. Unconverted lower alkane, corresponding alkene, unreacted oxygen, carbon dioxide, carbon monoxide, acetylene and inert diluent added to quench tower 20 exit through quench tower overhead line 110 and are directed into second reactor 25.

Second reactor 25, which can be variously positioned as described above, contains a catalyst material that includes CuO and ZnO, which removes all or part of the carbon monoxide, oxygen and acetylene. In second reactor 25, most or all of the unreacted oxygen and acetylene is consumed. The remaining unconverted lower alkane, corresponding alkene, unreacted oxygen (if present), all or part of the carbon dioxide, carbon monoxide (if present), acetylene (if present) and inert diluent are conveyed to amine wash tower 30 via line 115.

Any carbon dioxide present in line 115 is isolated by amine wash tower 30 and captured via carbon dioxide bottom outlet 120 and may be sold, or, alternatively, may be recycled back to ODH reactor 10 as described above. Constituents introduced into amine wash tower 30 via line 115, other than carbon dioxide, leave amine wash tower 30 through amine wash tower overhead line 130 and are passed through a dryer 40 before being directed to distillation tower 50, where C2/C2+ hydrocarbons are isolated and removed via C2/C2+ hydrocarbons bottom outlet 150. The remainder includes mainly C1 hydrocarbons, including remaining $N_2$ or $CH_4$ used as diluent that is in the vapor phase and carbon monoxide (if any), which leave distillation tower 50 via overhead stream 160.

In many embodiments, C2/C2+ hydrocarbons bottom outlet 150 is fed to a C2 splitter (not shown) that separates ethane from ethylene.

In many embodiments of the disclosure, the olefins produced using the one or more ODH reactors, or any of the processes or complexes described herein, can be used to make various olefin derivatives. Olefin derivatives include, but are not limited to polyethylene, polypropylene, ethylene oxide, propylene oxide, polyethylene oxide, polypropylene oxide, vinyl acetate, vinyl chloride, acrylic esters (e.g. methyl methacrylate), thermoplastic elastomers, thermoplastic olefins and blends and combinations thereof. Derivatives In many embodiments of the disclosure, the olefins produced using the one or more ODH reactors, or any of the processes or complexes described herein, can be used to make various olefin derivatives. Olefin derivatives include, but are not limited to polyethylene, polypropylene, ethylene oxide, propylene oxide, polyethylene oxide, polypropylene oxide, vinyl acetate, vinyl chloride, acrylic esters (e.g. methyl methacrylate), thermoplastic elastomers, thermoplastic olefins and blends and combinations thereof.

In many embodiments of the disclosure, ethylene and optionally α-olefins are produced in the one or more ODH reactors, or any of the processes or complexes described herein, and are used to make polyethylene. The polyethylene made from the ethylene and optional α-olefins described herein can include homopolymers of ethylene, copolymers of ethylene and α-olefins, resulting in HDPE, MDPE, LDPE, LLDPE and VLDPE.

The polyethylene produced using the ethylene and optional α-olefins described herein can be produced using any suitable polymerization process and equipment. Suitable ethylene polymerization processes include, but are not limited to gas phase polyethylene processes, high pressure polyethylene processes, low pressure polyethylene processes, solution polyethylene processes, slurry polyethylene processes and suitable combinations of the above arranged either in parallel or in series.

The present disclosure also contemplates use of various tools commonly used for chemical reactors, including flowmeters, compressors, valves, and sensors for measuring parameters such as temperature, pressure and flow rates. It is expected that the person of ordinary skill in the art would include these components as deemed necessary for operation.

A first aspect of the disclosure is directed to a method of converting one or more alkanes to one or more alkenes that includes:

a. providing a first stream comprising one or more alkanes and oxygen to an oxidative dehydrogenation reactor;

b. converting at least a portion of the one or more alkanes to one or more alkenes in the oxidative dehydrogenation reactor to provide a second stream exiting the oxidative dehydrogenation reactor comprising one or more alkanes, one or more alkenes, and one or both of oxygen and acetylene; and c. providing the second stream to a second reactor containing a catalyst comprising CuO and ZnO and reacting the second stream to provide a third stream exiting the second reactor comprising one or more alkanes, one or more alkenes, and lower or undetectable levels of oxygen and acetylene compared to the second stream.

A second aspect of the disclosure is directed to the first aspect where the one or more alkanes include ethane.

A third aspect of the disclosure is directed to the second aspect where the one or more alkenes includes ethylene.

A fourth aspect of the disclosure is directed to one or more of aspects one through three where the oxidative dehydrogenation reactor contains an oxidative dehydrogenation catalyst that includes one or more mixed metal oxides chosen from:

i) catalysts of the formula:

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals present in the catalyst;

ii) catalysts of the formula:

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to at least satisfy the valence state of the metals present in the catalyst;

iv) catalysts of the formula:

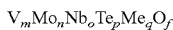

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals present in catalyst;

v) catalysts of the formula:

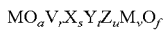

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the catalyst;

vi) a mixed metal oxide having the empirical formula:

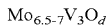

where d is a number to at least satisfy the valence of the metals in the catalyst.

vii) a mixed metal oxide having the empirical formula:

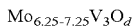

where d is a number to at least satisfy the valence of the metals in the catalyst.

A fifth aspect of the disclosure is directed to one or more of aspects one through four where the first stream includes one or more diluents, an oxygen containing gas and a gas containing one or more lower alkanes.

A sixth aspect of the disclosure is directed to one or more of aspects one through five where the second stream includes one or more unreacted lower alkanes; one or more lower alkenes; oxygen; one or more diluents; acetic acid; and water.

A seventh aspect of the disclosure is directed to one or more of aspects one through six where the oxidative dehydrogenation reactor includes a single fixed bed type reactor.

An eighth aspect of the disclosure is directed to one or more of aspects one through six where the oxidative dehydrogenation reactor includes a single fluidized bed type reactor and/or a moving bed reactor.

A ninth aspect of the disclosure is directed to one or more of aspects one through six where the oxidative dehydrogenation reactor includes a swing bed type reactor arrangement.

A tenth aspect of the disclosure is directed to one or more of aspects one through nine where an acetic acid scrubber is placed between the oxidative dehydrogenation reactor and the second reactor.

An eleventh aspect of the disclosure is directed to one or more of aspects one through ten where the temperature in the second reactor is from 100 to 200° C.

A twelfth aspect of the disclosure is directed to one or more of aspects one through eleven where the second stream includes carbon monoxide and the amount of carbon monoxide in the third stream is less than the amount of carbon monoxide in the second stream.

A thirteenth aspect of the disclosure is directed to one or more of aspects one through twelve where the gas hourly space velocity (GHSV) is from about 400 to about 30000 $h^{-1}$.

A fourteenth aspect of the disclosure is directed to one or more of aspects one through twelve where the weight hourly space velocity (WHSV) is from about 0.4 $h^{-1}$ to about 30 $h^{-1}$.

A fifteenth aspect of the disclosure is directed to one or more of aspects one through twelve the linear velocity is from about 5 cm/sec to about 500 cm/sec.

A sixteenth aspect of the disclosure is directed to a method of converting ethane to ethylene that includes: a) providing a first stream comprising ethane and oxygen to an oxidative dehydrogenation reactor; b) converting at least a portion of the ethane to ethylene in the oxidative dehydrogenation reactor to provide a second stream exiting the oxidative dehydrogenation reactor comprising ethane, ethylene, and one or both of oxygen and acetylene; and c) providing the second stream to a second reactor containing a catalyst comprising CuO and ZnO to provide a third stream exiting the second reactor comprising ethane, ethylene, and lower or undetectable levels of oxygen and acetylene compared to the second stream.

A seventeenth aspect of the disclosure is directed to aspect sixteen where the oxidative dehydrogenation reactor contains an oxidative dehydrogenation catalyst that includes one or more mixed metal oxides chosen from:

i) catalysts of the formula:

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the catalyst;

ii) catalysts of the formula:

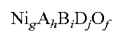

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$Mo_a E_k G_l O_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to at least satisfy the valence state of the metals in the catalyst;

iv) catalysts of the formula:

$$V_m Mo_n Nb_o Te_p Me_q O_f$$

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals in the catalyst;

v) catalysts of the formula:

$$Mo_a V_r X_s Y_t Z_u M_v O_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst;

vi) a mixed metal oxide having the empirical formula:

$$Mo_{6.5-7}V_3O_d$$

where d is a number to at least satisfy the valence of the metals in the catalyst.

vii) a mixed metal oxide having the empirical formula:

$$Mo_{6.25-7.25}V_3O_d$$

where d is a number to at least satisfy the valence of the metals in the catalyst.

An eighteenth aspect of the disclosure is directed to one or more of aspects sixteen and seventeen where the first stream includes one or more diluents, an oxygen containing gas and a gas containing ethane.

A nineteenth aspect of the disclosure is directed to one or more of aspects sixteen through eighteen where the second stream includes one or more of ethane; ethylene; oxygen; one or more diluents; acetic acid; and water.

A twentieth aspect of the disclosure is directed to one or more of aspects sixteen through nineteen where the oxidative dehydrogenation reactor includes a single fixed bed type reactor.

A twenty-first aspect of the disclosure is directed to one or more of aspects sixteen through eighteen where the oxidative dehydrogenation reactor includes a single fluidized bed type reactor and/or a moving bed reactor.

A twenty-second aspect of the disclosure is directed to one or more of aspects sixteen through eighteen where the oxidative dehydrogenation reactor includes a swing bed type reactor arrangement.

A twenty-third aspect of the disclosure is directed to one or more of aspects sixteen through twenty-two where an acetic acid scrubber is placed between the oxidative dehydrogenation reactor and the second reactor.

A twenty-fourth aspect of the disclosure is directed to one or more of aspects sixteen through twenty-three where the temperature in the second reactor is from 100 to 200° C.

A twenty-fifth aspect of the disclosure is directed to one or more of aspects sixteen through twenty-four where the gas hourly space velocity (GHSV) is from about 400 to about 30000 $h^{-1}$.

A twenty-sixth aspect of the disclosure is directed to one or more of aspects sixteen through twenty-four where the weight hourly space velocity (WHSV) is from about 0.4 $h^{-1}$ to about 30 $h^{-1}$.

A twenty-seventh aspect of the disclosure is directed to one or more of aspects sixteen through twenty-four where the linear velocity is from about 5 cm/sec to about 500 cm/sec.

A twenty-eighth aspect of the disclosure is directed to a chemical complex for oxidative dehydrogenation of lower alkanes, the chemical complex includes in cooperative arrangement:

i) at least one oxidative dehydrogenation reactor, comprising an oxidative dehydrogenation catalyst and designed to accept, optionally in the presence of an diluent, an oxygen containing gas and a lower alkane containing gas, and to produce a product stream comprising the corresponding alkene and one or more of:
  a. unreacted lower alkane;
  b. oxygen;
  c. diluent;
  d. acetylene;
  e. oxygenates; and
  f. water;
ii) a quench tower for quenching the product stream and for removing water and soluble oxygenates from said product stream;
iii) a second reactor containing a catalyst comprising CuO and ZnO to provide a second product stream exiting the second reactor comprising unreacted lower alkane, alkene, and lower or undetectable levels of oxygen and acetylene compared to the product stream;
iv) an optional amine wash for removing any carbon dioxide from said second product stream;
v) a dryer for removal of water from said second product stream; and
vi) a distillation tower for removing C2/C2+ hydrocarbons from said second product stream to produce an overhead stream enriched with C1 hydrocarbons, wherein the components in i) through vi) are connected in series in the sequence described.

A twenty-ninth aspect of the disclosure is directed to the twenty-eighth aspect where a non-flammable liquid flooded gas mixer for premixing the oxygen containing gas, the lower alkane containing gas and heat removal gases prior to introduction into the at least one oxidative dehydrogenation reactor.

A thirtieth aspect of the disclosure is directed to one or more of aspects twenty-eight and twenty nine where the oxidative dehydrogenation catalyst includes a mixed metal oxide chosen from:

i) catalysts of the formula:

$$Mo_a V_b Te_c Nb_d Pd_e O_f$$

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the catalyst;

ii) catalysts of the formula:

$$Ni_g A_h B_i D_j O_f$$

wherein: g is a number from 0.1 to 0.9, in some cases from 0.3 to 0.9, in other cases from 0.5 to 0.85, in some instances 0.6 to 0.8; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof; B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof; D is chosen from Ca, K, Mg, Li, Na, Sr, Ba, Cs, and Rb and mixtures thereof; and O is oxygen;

iii) catalysts of the formula:

$$MO_a E_k G_i O_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof; a=1; k is 0 to 2; l=0 to 2, with the proviso that the total value of l for Co, Ni, Fe and mixtures thereof is less than 0.5; and f is a number to at least satisfy the valence state of the catalyst;

iv) catalysts of the formula:

$$V_m MO_n Nb_o Te_p Me_q O_f$$

wherein: Me is a metal chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the catalyst;

v) catalysts of the formula:

$$MO_a V_r X_s Y_t Z_u M_v O_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the catalyst; and vi) a mixed metal oxide having the empirical formula:

$$Mo_{6.5-7} V_3 O_d$$

where d is a number to at least satisfy the valence of the metals in the catalyst.

vii) a mixed metal oxide having the empirical formula:

$$Mo_{6.25-7.25} V_3 O_d$$

where d is a number to at least satisfy the valence of the metals in the catalyst.

In an example aspect of the disclosure, the at least one oxidative dehydrogenation reactor comprises a single fixed bed type reactor.

A thirty-first aspect of the disclosure is directed to one or more of aspects twenty-eight through thirty where the at least one oxidative dehydrogenation reactor includes a single fluidized bed type reactor and/or a moving bed reactor.

A thirty-second aspect of the disclosure is directed to one or more of aspects twenty-eight through thirty where the at least one oxidative dehydrogenation reactor includes a swing bed type reactor arrangement.

A thirty-third aspect of the disclosure is directed to one or more of aspects twenty-eight through thirty where the at least one oxidative dehydrogenation reactor includes more than one oxidative dehydrogenation reactor, each including the same or different oxidative dehydrogenation catalyst, connected in series, and wherein the product stream from each oxidative dehydrogenation reactor except the last oxidative dehydrogenation reactor in the series is fed into a downstream oxidative dehydrogenation reactor.

A thirty-fourth aspect of the disclosure is directed to one or more of aspects twenty-eight through thirty where the at least one oxidative dehydrogenation reactor includes more than one oxidative dehydrogenation reactor connected in parallel and each including the same or different oxidative dehydrogenation catalyst.

A thirty-fifth aspect of the disclosure is directed to one or more of aspects twenty-eight through thirty-four where the chemical complex further includes at least one heat exchanger immediately upstream of said quench tower.

A thirty-sixth aspect of the disclosure is directed to one or more of aspects twenty-eight through thirty-six where the chemical complex further includes a caustic wash tower immediately downstream of said amine wash tower.

A thirty-seventh aspect of the disclosure is directed to one or more of aspects twenty-eight through thirty-six where the C2/C2+ hydrocarbons leave the distillation tower and are directed to a second distillation tower for separation of unreacted lower alkane and corresponding alkene into an unreacted lower alkane stream and a corresponding alkene stream.

A thirty-eighth aspect of the disclosure is directed to aspect thirty seven where the second distillation tower further provides for separation of the C2/C2+ hydrocarbons portion of the product stream into an unreacted lower alkane stream and a corresponding alkene stream.

A thirty-ninth aspect of the disclosure is directed to one or more of aspects thirty-seven and thirty-eight where the unreacted lower alkane stream is directed back to said at least one oxidative dehydrogenation reactor as part of the lower alkane containing gas.

A fortieth aspect of the disclosure is directed to one or more of aspects twenty-eight through thirty-nine where the oxygenates include one or more selected from acetic acid, ethanol, acrylic acid, acetaldehyde, maleic acid and maleic anhydride.

A forty-first aspect of the disclosure is directed to one or more of aspects twenty-eight through forty where the gas hourly space velocity (GHSV) is from about 400 to about 30000 $h^{-1}$.

A forty-second aspect of the disclosure is directed to one or more of aspects twenty-eight through forty where the weight hourly space velocity (WHSV) is from about 0.4 $h^W$ to about 30 $h^{-1}$.

A forty-third aspect of the disclosure is directed to one or more of aspects twenty-eight through forty where the linear velocity is from about 5 cm/sec to about 500 cm/sec.

EXAMPLES

The following examples are intended to aid in understanding the present disclosure, however, in no way, should these examples be interpreted as limiting the scope thereof.

The ODH catalyst was prepared as follows. A solution of $(NH_4)_6 Mo_7 O_{24} \cdot 4H_2O$ (44.20 g, 35.77 mmol, white solid) in 600 mL of distilled water was prepared in a 2-L RBF equipped with a magnetic stir bar. A solution of $VOSO_4 \cdot 3.46 H_2O$ (14.07 g, 62.95 mmol, bright blue solid) in 600 mL of distilled water was prepared in a 1-L beaker equipped with a magnetic stir bar. Both solutions were stirred in a 60° C. water bath until homogeneous. The blue vanadium solution was then added to the clear colorless molybdenum solution. This resulted in a dark purple solution with a fine suspension. Sodium dodecyl sulfate (SDS)

(13.57 g, 47.06 mmol, white solid) was added to the reaction mixture. The purple slurry was left to stir at 60° C. for 1 hour.

The reaction mixture was transferred to a glass liner, with a total volume of about 1380 mL measured after rinsing. The liner was loaded into a 2-L pressure reactor (Parr Instrument Company, Moline, IL) and the gap filled with distilled water. The reactor was sealed and the head space evacuated and backfilled with nitrogen gas 10× times. The headspace was left under 15 psig nitrogen gas and sealed. The reactor was transferred to a programmable oven and heated for 24 hours at 230° C. (1-hour ramp to 230° C., 24-hour cooling ramp back to room temperature). Once cooled to room temperature, the reactor was vented, and the contents filtered using a Buchner funnel and 4 quantitative filter papers. The oily mother liquor was decanted off and the filter papers changed. The filter cake was rinsed with 1250 mL of distilled water. The filtrate was a dark blue color and the product was a charcoal/grey purple color.

The filter cake was dried in an oven at 90° C. overnight with 15.29 g of product being recovered (37% estimated yield). The uncalcined catalyst was broken up with a spatula and then loaded into a programmable muffle furnace. The program was set to ramp over one hour to 280° C. and held there for 9 hours, before cooling back to room temperature naturally. This air treated product was ground with mortar and pestle and submitted for CHN analysis. The carbon and nitrogen content were found to be less than 1 wt. %. The material was loaded into a quartz boat and centered in the quartz tube of the QRU furnace. The quartz tube was purged (400 sccm) with bulk nitrogen for 8 hours, after which the nitrogen feed was fed through an oxygen scrubbing bed to further purify the nitrogen to less than 4 ppmv oxygen. This ultra-high purity (UHP) nitrogen was purged through the quartz tube overnight. The next morning, the furnace was turned on and heated to 400° C. over a 4-hour ramp. The catalyst was calcined at 400° C. for 2 hours and then cool to ambient temperature naturally.

5.0 g of calcined catalyst (92 wt. %) and 0.44 g of beryllium oxide (8 wt. %) were placed into a 100 mL beaker (92%). About 30 mL of distilled water was added to the beaker and stirred manually. This beaker was placed into an oil bath at about 100° C. and an overhead stirrer was set up so the paddle was just off the bottom of the beaker. The mixture was stirred at 80 rpm for about 1.5 hours until it formed a paste and the beaker with the paste was placed in an oven at 90° C. to dry overnight. The solid catalyst chunk was broken up with a spatula and was placed in a muffle furnace at 350° C. for 3.5 hours to form the ODH catalyst.

The catalyst composition for the second reactor in these examples is the reduced form of an oxide precursor composition containing 70 wt. % CuO, 20 wt. % ZnO and 10 wt. % $ZrO_2$. For production of this oxide precursor composition, a Cu—Zn—Zr nitrate solution (metal content 15.2 wt. %, Cu:Zn:Zr ratio corresponding to a $CuO:ZnO:ZrO_2$ weight ratio of 7:2:1) was precipitated with soda solution (20 wt. %) at pH 6.5 and 70° C. After completion of precipitation, the suspension was stirred for a further 120 minutes at pH 6.5 and 70° C. Next, the solution was filtered, and the filter cake washed free of nitrate with demineralized water and dried at 120° C. The dried powder was calcined at 300° C. for 240 minutes in a forced air oven to form the second reactor catalyst.

Figure 2:
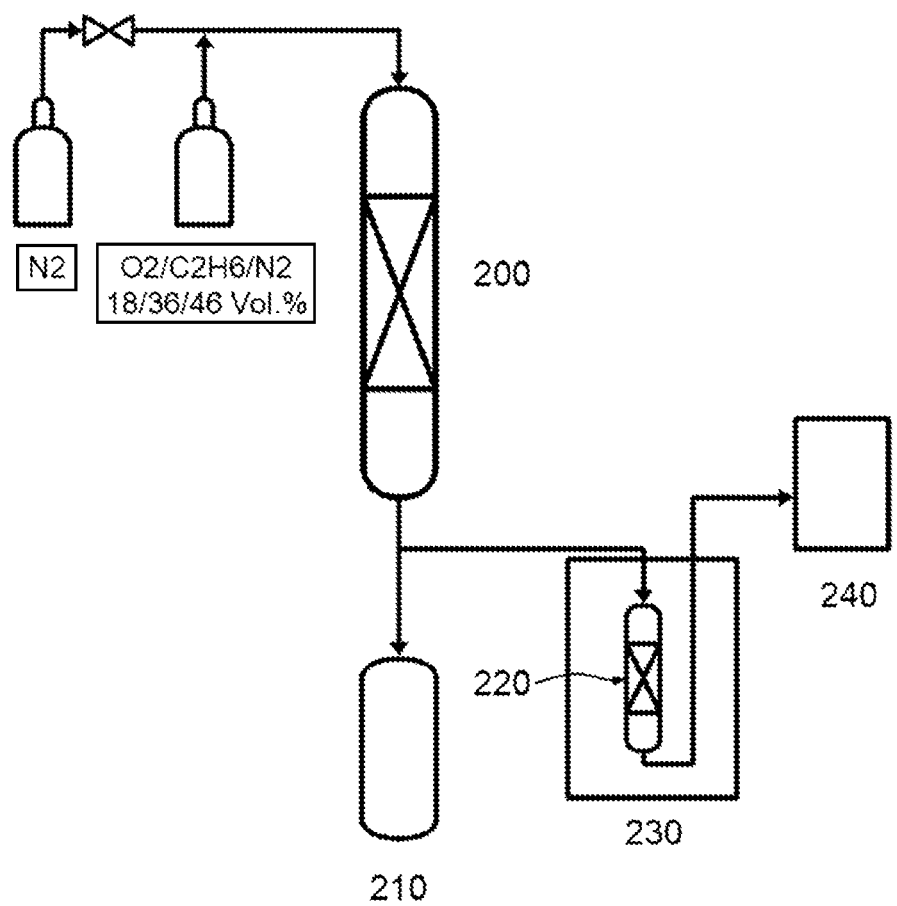
FIG. 2 is a schematic representation of experimental setup used to produce results shown in Table 1.

The ODH catalyst was evaluated in an apparatus depicted in FIG. 2. ODH reactor 200 was a lab scale dehydrogenation reactor (ODH micro reactor unit).

The feed to ODH reactor 200 included oxygen, ethane and nitrogen at a weight ratio of 18 vol %/36 vol %/46 vol % respectively at 8.4 psig and a gas flow rate of 32.8 sccm through ⅛ inch outside diameter tubing. The ODH catalyst/beryllium oxide described above was placed in ODH reactor 200 and the gas feed was processed through ODH reactor 200 at 327° C. The effluent from ODH reactor 200 was passed through condenser 210 where an aqueous solution containing 18.5 wt. % acetic acid was condensed and the remaining effluent gas was passed to second reactor 220 at 14 psig.

Second reactor 220 was placed in temperature control oven 230 and loaded with 2 g of the second reactor catalyst. Effluent gas from condenser 210 was introduced into the second reactor 220 at a pressure of 14 psig and a flow rate of 32.8 sccm, and contacted the second reactor catalyst within the second reactor 220 at various temperatures before exiting second reactor 220 at ambient pressure. Samples of effluent gas after leaving second reactor 220 were collected and subsequently evaluated in gas chromatograph 240.

Table 1 outlines the composition of samples of effluent gas taken after leaving the second reactor. Samples include 2 original samples taken when temperature control oven 320 was set to "off", representing ambient temperature. Subsequent samples were taken after the temperature was ramped up to specific temperatures and held at those temperatures for the times indicated.

TABLE 1

Effluent Gas Composition (vol %) as a Function of Temperature and Time

| | $C_2H_6$ (vol %) | $C_2H_4$ (vol %) | $O_2$ (vol %) | $CO_2$ (vol %) | $N_2$ (vol %) | CO (vol %) | H2 (vol %) | $CH_4$ (vol %) | $C_2H_2$ (vol %) |
|---|---|---|---|---|---|---|---|---|---|
| Feed | 21.21 | 14.59 | 0.45 | 2.36 | 56.31 | 5.05 | 0.00 | 0.02 | 0.02 |
| Feed | 21.14 | 14.54 | 0.42 | 2.37 | 56.41 | 5.08 | 0.00 | 0.02 | 0.02 |
| | | | | Product | | | | | |
| 100° C. (1.5 hr) | 21.38 | 14.63 | 0.17 | 2.40 | 56.33 | 5.06 | 0.00 | 0.02 | 0.01 |
| 120° C. (2.5 hr) | 21.26 | 14.54 | 0.14 | 2.56 | 56.52 | 4.95 | 0.00 | 0.02 | 0.00 |
| 150° C. (3 hr) | 21.54 | 14.68 | 0.03 | 6.78 | 56.59 | 0.35 | 0.00 | 0.02 | 0.00 |
| 150° C. (3.5 hr) | 21.99 | 14.28 | 0.03 | 6.97 | 56.56 | 0.14 | 0.00 | 0.02 | 0.00 |
| 150° C. (14.5 hr) | 21.78 | 14.21 | 0.03 | 2.48 | 56.40 | 5.06 | 0.02 | 0.02 | 0.00 |
| 150° C. (14.5 hr) | 21.78 | 14.21 | 0.03 | 2.45 | 56.43 | 5.06 | 0.02 | 0.02 | 0.00 |
| 150° C. (15 hr) | 21.64 | 14.11 | 0.03 | 2.50 | 56.60 | 5.08 | 0.02 | 0.02 | 0.00 |

The data in Table 1 demonstrate that the second reactor catalyst removes O2, CO, and acetylene at temperatures of higher than 120° C. It is also clear from the data shown in Table 1 that all the compounds are not being chemosorbed but rather reacted either with oxygen from the catalyst or in the gas stream. The constant presence of oxygen in the feed stream was sufficient to oxidize all of the acetylene, which led to continuous removal of acetylene and O2, even after the catalyst material was depleted of chemosorbed oxygen.

While the present disclosure has been particularly set forth in terms of specific embodiments thereof, it will be understood in view of the instant disclosure that numerous variations upon the disclosure are now enabled yet reside within the scope of the disclosure. Accordingly, the disclosure is to be broadly construed and limited only by the scope and spirit of the claims now appended hereto.

INDUSTRIAL APPLICABILITY

The process is applicable for the oxidative dehydrogenation (ODH) of lower alkanes. The process is applicable for controlling the carbon monoxide, oxygen, and/or acetylene output levels from an ODH process.

The invention claimed is:

1. A method of converting an alkane to an alkene comprising:
providing a first stream comprising an alkane, carbon dioxide, and oxygen to an oxidative dehydrogenation reactor containing an oxidative dehydrogenation catalyst supported on or agglomerated with a binder comprising AlO(OH) or $Nb_2O_5$;
converting at least a portion of the alkane to the alkene in the oxidative dehydrogenation reactor in a carbon dioxide negative process to provide a second stream exiting the oxidative dehydrogenation reactor comprising the alkanes, the alkene, and oxygen or acetylene or both, wherein an amount of carbon dioxide in the second stream exiting the oxidative dehydrogenation reactor is in a range of from about −5 vol % to about −10 vol % of an amount of carbon dioxide in the first stream provided to the oxidation dehydrogenation reactor; and
providing the second stream to a second reactor containing a catalyst comprising CuO and ZnO and reacting the second stream to provide a third stream exiting the second reactor comprising the alkane, the alkene, and a lower level of oxygen, a lower level of acetylene, or lower levels of both oxygen and acetylene compared to the second stream.

2. The method according to claim 1, wherein the alkane comprises ethane.

3. The method according to claim 1, wherein the alkene comprises ethylene.

4. The method according to claim 1, wherein the oxidative dehydrogenation catalyst comprises a mixed metal oxide chosen from:
a catalyst of the formula:

$$Mo_aV_bTe_cNb_dPd_eO_f$$

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the metals present in the catalyst;
a catalyst of the formula:

$$Ni_gA_hB_iD_jO_f$$

wherein: g is a number from 0.1 to 0.9; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof, B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof, D is chosen from Ca, K, Mg, Li, Na, Sr, Ba, Cs, and Rb and mixtures thereof, and O is oxygen;
a catalyst of the formula:

$$Mo_aE_kG_lO_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof, a=1; k is 0 to 2; l=0 to 2, with the proviso that the total value of 1 for Co, Ni, Fe and mixtures thereof is less than 0.5; and f is a number to at least satisfy the valence state of the metals present in the catalyst;
a catalyst of the formula:

$$V_mMo_nNb_oTe_pMe_qO_f$$

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals present in catalyst;
a catalyst of the formula:

$$MO_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the catalyst;
a mixed metal oxide having the empirical formula:

$$Mo_{6.5-7}V_3O_d$$

where d is a number to at least satisfy the valence of the metals in the catalyst; and
a mixed metal oxide having the empirical formula:

$$Mo_{6.25-7.25}V_3O_d$$

where d is a number to at least satisfy the valence of the metals in the catalyst.

5. The method according to claim 1, wherein the first stream comprises a diluent, an oxygen containing gas, and a gas containing a lower alkane.

6. The method according to claim 1, wherein the second stream comprises: an unreacted lower alkane; a lower alkene; oxygen; a diluent; acetic acid; and water.

7. The method according to claim 1, wherein the oxidative dehydrogenation reactor comprises a single fixed bed type reactor.

8. The method according to claim 1, wherein the oxidative dehydrogenation reactor comprises a single fluidized bed type reactor and/or a moving bed reactor.

9. The method according to claim 1, wherein the oxidative dehydrogenation reactor comprises a swing bed type reactor arrangement.

10. The method according to claim 1, wherein the second stream exiting the oxidative dehydrogenation reactor is provided to an acetic acid scrubber to remove oxygenates prior to being provided to the second reactor.

11. The method according to claim 1, wherein the second stream includes carbon monoxide and the amount of carbon monoxide in the third stream is less than the amount of carbon monoxide in the second stream.

12. The method according to claim 1, wherein the gas hourly space velocity (GHSV) of the first stream in the oxidative dehydrogenation reactor is from about 400 to about 30000 $h^{-1}$.

13. The method according to claim 1, wherein the weight hourly space velocity (WHSV) of the first stream in the oxidative dehydrogenation reactor is from about 0.4 $h^{-1}$ to about 30 $h^{-1}$.

14. The method according to claim 1, wherein the linear velocity of the first stream in the oxidative dehydrogenation reactor is from about 5 cm/sec to about 500 cm/sec.

15. A method of converting ethane to ethylene comprising:
providing a first stream comprising ethane, carbon dioxide, and oxygen to an oxidative dehydrogenation reactor containing an oxidative dehydrogenation catalyst supported on or agglomerated with a binder comprising AlO(OH) or $Nb_2O_5$;
converting at least a portion of the ethane to ethylene in the oxidative dehydrogenation reactor in a carbon dioxide negative process to provide a second stream exiting the oxidative dehydrogenation reactor comprising ethane, ethylene, and oxygen or acetylene or both, wherein an amount of carbon dioxide in the second stream exiting the oxidative dehydrogenation reactor is in a range of from about −5 vol % to about −10 vol % of an amount of carbon dioxide in the first stream provided to the oxidation dehydrogenation reactor; and
providing the second stream to a second reactor containing a catalyst comprising CuO and ZnO to provide a third stream exiting the second reactor comprising ethane, ethylene, and a lower level of oxygen, a lower level of acetylene, or lower levels of both oxygen and acetylene compared to the second stream.

16. The method according to claim 15, wherein the oxidative dehydrogenation catalyst comprises a mixed metal oxide chosen from:
a catalyst of the formula:

$$Mo_aV_bTe_cNb_dPd_eO_f$$

wherein: a, b, c, d, e and f are the relative atomic amounts of the elements Mo, V, Te, Nb, Pd and O, respectively; and when a=1, b=0.01 to 1.0, c=0.01 to 1.0, d=0.01 to 1.0, 0.00≤e≤0.10 and f is a number to at least satisfy the valence state of the catalyst;
a catalyst of the formula:

$$Ni_gA_hB_iD_jO_f$$

wherein: g is a number from 0.1 to 0.9; h is a number from 0.04 to 0.9; i is a number from 0 to 0.5; j is a number from 0 to 0.5; and f is a number to at least satisfy the valence state of the catalyst; A is chosen from Ti, Ta, V, Nb, Hf, W, Y, Zn, Zr, Si and Al or mixtures thereof, B is chosen from La, Ce, Pr, Nd, Sm, Sb, Sn, Bi, Pb, Tl, In, Te, Cr, Mn, Mo, Fe, Co, Cu, Ru, Rh, Pd, Pt, Ag, Cd, Os, Ir, Au, Hg, and mixtures thereof, D is chosen from Ca, K, Mg, Li, Na, Sr, Ba, Cs, and Rb and mixtures thereof, and O is oxygen;
a catalyst of the formula:

$$Mo_aE_kG_lO_f$$

wherein: E is chosen from Ba, Ca, Cr, Mn, Nb, Ta, Ti, Te, V, W and mixtures thereof; G is chosen from Bi, Ce, Co, Cu, Fe, K, Mg, V, Ni, P, Pb, Sb, Si, Sn, Ti, U, and mixtures thereof, a=1; k is 0 to 2; l=0 to 2, with the proviso that the total value of l for Co, Ni, Fe and mixtures thereof is less than 0.5; and f is a number to at least satisfy the valence state of the metals in the catalyst;
a catalyst of the formula:

$$V_mMo_nNb_oTe_pMe_qO_f$$

wherein: Me is chosen from Ta, Ti, W, Hf, Zr, Sb and mixtures thereof; m is from 0.1 to 3; n is from 0.5 to 1.5; o is from 0.001 to 3; p is from 0.001 to 5; q is from 0 to 2; and f is a number to at least satisfy the valence state of the metals in the catalyst;
a catalyst of the formula:

$$Mo_aV_rX_sY_tZ_uM_vO_f$$

wherein: X is at least one of Nb and Ta; Y is at least one of Sb and Ni; Z is at least one of Te, Ga, Pd, W, Bi and Al; M is at least one of Fe, Co, Cu, Cr, Ti, Ce, Zr, Mn, Pb, Mg, Sn, Pt, Si, La, K, Ag and In; a=1.0 (normalized); r=0.05 to 1.0; s=0.001 to 1.0; t=0.001 to 1.0; u=0.001 to 0.5; v=0.001 to 0.3; and f is a number to at least satisfy the valence state of the metals in the catalyst;
a mixed metal oxide having the empirical formula:

$$Mo_{6.5-7}V_3O_d$$

where d is a number to at least satisfy the valence of the metals in the catalyst
a mixed metal oxide having the empirical formula:

$$Mo_{6.25-7.25}V_3O_d$$

where d is a number to at least satisfy the valence of the metals in the catalyst.

17. The method according to claim 15, wherein the first stream comprises a diluent, an oxygen containing gas, and a gas containing ethane.

18. The method according to claim 15, wherein the second stream comprises the ethane, ethylene, oxygen, a diluent, acetic acid, and water.

* * * * *